United States Patent
Faupel et al.

(10) Patent No.: US 9,782,482 B2
(45) Date of Patent: Oct. 10, 2017

(54) TRANSDERMAL DEVICE FOR THE CONTROLLED ADMINISTRATION OF AT LEAST ONE ACTIVE INGREDIENT TO A PATIENT

(71) Applicant: RHENOVIA PHARMA S.A.S., Mulhouse (FR)

(72) Inventors: Michel Faupel, Eschentzwiller (FR); Serge Bischoff, Robion (FR); Florian George, Strasbourg (FR); Peter Stark, Schoenenbuch (CH)

(73) Assignee: Therascape, Strasbourg (FR)

( * ) Notice: Subject to any disclaimer, the term of this patent is extended or adjusted under 35 U.S.C. 154(b) by 688 days.

(21) Appl. No.: 14/373,923

(22) PCT Filed: Jan. 30, 2013

(86) PCT No.: PCT/FR2013/000028
§ 371 (c)(1),
(2) Date: Jul. 23, 2014

(87) PCT Pub. No.: WO2013/114011
PCT Pub. Date: Aug. 8, 2013

(65) Prior Publication Data
US 2015/0018749 A1    Jan. 15, 2015

(30) Foreign Application Priority Data

Jan. 30, 2012 (FR) ...................... 12 50851

(51) Int. Cl.
*A61K 41/00* (2006.01)
*A61K 9/00* (2006.01)
(Continued)

(52) U.S. Cl.
CPC ........ *A61K 41/0057* (2013.01); *A61K 9/0009* (2013.01); *A61K 9/703* (2013.01);
(Continued)

(58) Field of Classification Search
CPC .... A61K 9/0009; A61K 9/7023; A61K 9/703; A61K 9/7084; A61K 9/7092; A61K 41/0057
See application file for complete search history.

(56) References Cited

U.S. PATENT DOCUMENTS 5,464,387 A * 11/1995 Haak .................... A61K 9/0009
                                                                        604/20
5,505,720 A *  4/1996 Walters ............. A61F 13/47236
                                                                        604/358
(Continued)

FOREIGN PATENT DOCUMENTS

WO       2004/060447 A2    7/2004

OTHER PUBLICATIONS

Noel, Scott P. et al.: "Chitosan Sponges to Locally Deliver Amikacin and Vancomycin: A Pilot In Vitro Evaluation", Clinical Orthopedics and Related Research, Aug. 2010, vol. 468, No. 8, pp. 2074-2080.
(Continued)

*Primary Examiner* — Andrew Gilbert
(74) *Attorney, Agent, or Firm* — Davis & Bujold PLLC; Michael J. Bujold

(57) ABSTRACT

A transdermal device (1) comprising at least one substrate (2) arranged to be applied against the dermal surface or the mucous membrane. The at least one active ingredient is grafted to the substrate (2) by at least one photolabile ligand, and at least one light source (11) operated by a control mechanism arranged to generate light pulses, of a predetermined wavelength, intended to break covalent bonds between the active ingredient and the ligand in order to release the active ingredient from the substrate (2). The substrate (2) comprises at least one porous matrix (6) with a three-dimensional structure comprising a plurality of pits (7) organized in a sponge-like fashion and constructed of a
(Continued)

polymer chosen between chitin and chitosan, and the matrix (6) defines at least one three-dimensional tank (8). The active ingredient is contained and grafted by the ligand.

18 Claims, 2 Drawing Sheets

(51) Int. Cl.
 *A61K 9/70* (2006.01)
 *A61N 5/06* (2006.01)
(52) U.S. Cl.
 CPC .......... *A61K 9/7023* (2013.01); *A61K 9/7084* (2013.01); *A61K 9/7092* (2013.01); *A61N 5/0613* (2013.01); *A61N 2005/0626* (2013.01); *A61N 2005/0652* (2013.01)

(56) References Cited

U.S. PATENT DOCUMENTS

| | | | | |
|---|---|---|---|---|
| 6,068,853 | A * | 5/2000 | Giannos | A61K 9/7084 424/447 |
| 7,666,179 | B2 * | 2/2010 | Tenney | A61L 27/54 604/19 |
| 7,991,464 | B2 * | 8/2011 | Schmitt | A61K 9/0009 604/20 |
| 8,206,326 | B2 * | 6/2012 | Schafer | A61M 37/0092 601/1 |
| 8,372,128 | B2 * | 2/2013 | Reuben | A61F 13/0203 607/88 |
| 9,289,584 | B2 * | 3/2016 | Chiao | A61M 31/002 |
| 2002/0099359 | A1 * | 7/2002 | Santini, Jr. | A61F 9/0017 604/521 |
| 2006/0024358 | A1 | 2/2006 | Santini, Jr. et al. | |
| 2006/0173514 | A1 * | 8/2006 | Biel | A61F 13/023 607/88 |
| 2009/0162249 | A1 * | 6/2009 | Hood | A61M 5/14276 422/105 |
| 2010/0239647 | A1 * | 9/2010 | Byrne | A61K 9/0009 424/449 |
| 2011/0264174 | A1 * | 10/2011 | McNeill | A61N 5/062 607/88 |
| 2012/0289885 | A1 * | 11/2012 | Cottrell | A61N 5/0616 604/20 |
| 2013/0116616 | A1 * | 5/2013 | Buchholz | A61N 5/0616 604/20 |

OTHER PUBLICATIONS

International Search Report Corresponding to PCT/FR2013/000028 mailed Jul. 10, 2013.

* cited by examiner

TRANSDERMAL DEVICE FOR THE CONTROLLED ADMINISTRATION OF AT LEAST ONE ACTIVE INGREDIENT TO A PATIENT

This application is a National Stage completion of PCT/FR2013/000028 filed Jan. 30, 2013, which claims priority from French patent application serial no. 12/50851 filed Jan. 30, 2012.

FIELD OF THE INVENTION

The present invention relates to a transdermal device for the controlled administration of at least one active ingredient to a patient through a dermal surface or a mucous membrane, said device comprising at least one substrate, arranged to be applied against said dermal surface or said mucous membrane, said at least one active ingredient being grafted to said substrate by means of at least one photolabile ligand, said transdermal device comprising in addition at least one light source operated by control means arranged to generate light pulses of a predetermined wavelength intended to break said at least one ligand and release said at least one active ingredient from said substrate.

BACKGROUND OF THE INVENTION

Transdermal patches are known and used since the years 1979 to administrate to patients, by means of diffusion through the dermis, a certain dose of active ingredient into the body via the blood or the lymph thanks to body heat and to the solubility of the active ingredient. One of the advantages of the transdermal administration of a drug with respect to the other oral, topical or inhalation, etc., types of administration is the fact that it allows a slow release of the drug. However, the skin, which forms an efficient barrier, is a limitation for this method of administration. Nevertheless, a wide variety of active ingredients can be delivered transdermally. Another advantage of this method of administration lies in the fact that it takes place automatically, without any intervention of the patient and without any risk of omission or overdosage. A further advantage is the significant reduction of the adverse effects linked with the other methods of administration of drugs, orally, by inhalation, etc. And another advantage is the reduction of the active ingredients required to produce the same effects, as they are diffused directly in the body via the blood, the lymph or the tissues, without having to pass through other organs, in particular the digestive tract.

The commercially available transdermal patches generally comprise a package that protects the patch during storage and that is removed prior to use, a patch comprising a side intended to be applied against the skin and which contains a dose of active ingredient or drug in solution to pass through the skin, and a watertight back that protects the patch against the environment, an adhesive used both to hold the patch components together and to fasten the patch onto the skin, and a membrane laid over the patch side in contact with the skin to control the release of the drug.

The market is dominated by the so-called passive transdermal patches, which means that these diffuse continuously a determined quantity of active ingredients for a determined duration from the moment the patch is applied on the skin. This type of transdermal patches is indicated to treat in particular pain, tobacco dependence and the disorders related to menopause in women.

Other so-called active transdermal patches have been developed to control the diffusion of the active ingredients through the skin using various control means such as heat, micro-currents, light, micro-injection. Likewise, most of the transdermal patches are designed to diffuse one single active ingredient. In very specific cases, such as menopause treatment, certain transdermal patches diffuse a combination of two active ingredients. Furthermore, in all known transdermal patches, the active ingredient is stored directly in the substrate, which is in constant contact with the skin and which is a significant cause of allergy, independently of the active ingredient itself. In addition, the active ingredient can migrate or degrade when in contact with the skin.

One constantly tries to reduce the size of the transdermal patch, improve its performances in terms of therapeutic efficacy and personalize it to adapt the dosage to the patient in function of the disease(s) to be treated.

One of the solutions is in particular described in patent U.S. Pat. No. 7,991,464, which offers a transderrnal patch wherein the active ingredient is bonded to the substrate of the transdermal patch by means of a photolabile bond sensitive to the action of an evanescent field produced by a light pulse in the ultraviolet range through the polymer substrate that forms a light guide. The light pulse that releases the active ingredient is generated by a light-emitting diode (LED) operated by an electronic circuit and arranged opposite to the edge of the substrate in order to diffuse the evanescent field in the thickness of said substrate. A prior software-performed reaction kinetics study allows determining the illumination time required to release a determined quantity of active ingredient. This data is processed by the microprocessor integrated in the electronic circuit. This technology allows personalizing the dosage of said patch and correcting the dosage if necessary.

However, this technology is limited to the delivery of one single active ingredient. It is also limited in terms of quantity of stored active ingredient, as the limit is imposed by the two-dimensional surface of the transdermal patch. Moreover, not all molecules of the active ingredients liable to be used are compatible with the photolabile ligands, which considerably restricts the therapeutic applications of such transdermal patch.

Publication US 2006/0024358 describes a transdermal device comprising several tanks with the purpose of releasing various active ingredients in a way that can be controlled and modified. These tanks are closed by a lid arranged to disintegrate electrically or thermally and release the active ingredient towards the skin of the patient through a matrix serving as a vehicle and a permeable adhesive membrane. Nevertheless, these tanks are arranged on a same plane, thus limiting the quantity of active ingredient that can be stored.

Publication WO 2004/060447 describes a transdermal device wherein the active ingredients are encapsulated in microparticles or nanoparticles dispersed in a monolithic matrix such as a hydrogel. The active ingredients are released by causing the envelope of the microparticles to break using ultrasound and/or heat. However, this device does not comprise several tanks for storing various active ingredients.

Publication US 2006/0173514 relates to an electrotherapy wound treatment. The dressing comprises in particular a matrix made out of a hydrogel or a foam and a light source coupled with a battery. It is applied on the wound after having applied a photosensitive active ingredient on said wound. It therefore does not contain active ingredients stored in tanks and diffused in a controlled way.

Publication U.S. Pat. No. 5,464,387 describes an iontophoresis transdermal device using two electrodes coupled each to a tank of active ingredients and connected serially with an energy source. It furthermore comprises a passive tank in the form of a hydrogel arranged to release continuously an active ingredient by means of simple diffusion. This device does not comprise tanks allowing storing a large quantity of active ingredients.

Therefore the existing solutions are not satisfactory.

SUMMARY OF THE INVENTION

The present invention aims to overcome these disadvantages by offering an improved transdermal device wherein it is possible for example to deliver successively same dosages or different dosages of a same active ingredient, or jointly or successively at least two different active ingredients, in order to increase the therapeutic effects by playing on the synergy of the active ingredients to achieve a much better result than the sum of the effects of each active ingredient taken individually. Another goal of the invention is to be able to store a markedly larger quantity of active ingredients than with the patches of the prior art. A further goal of the invention is to be able to administer any kind of active ingredient, without limitation linked with the compatibility with the photolabile ligands used. Another goal of the invention is to control efficiently the quantity of the active ingredient(s) administered, bringing considerable improvement in the treatment of diseases by reducing to the minimum the administered quantity for a maximum therapeutic effect, resulting in reduced or even in no side effects.

To that purpose, the invention relates to a transdermal device of the kind described in the preamble, characterized in that said substrate comprises at least one porous matrix with a three-dimensional structure comprising a plurality of pits, organized in a sponge-like fashion and constructed of a polymer chosen between chitin and chitosan, said matrix defining at least one three-dimensional tank wherein said at least one active ingredient is contained and grafted.

In compliance with an embodiment variant, said substrate comprises a plurality of matrices arranged to define each a tank able to contain each a same concentration of a same active ingredient, or different concentrations of a same active ingredient or different active ingredients.

According to an advantageous characteristic of the invention, said substrate forms an interchangeable module connected with said device by means of a non-permanent adhesive.

In compliance with another embodiment variant of the device, said at least one active ingredient is encapsulated in at least one type of nanoparticles bonded with said at least one ligand, which is grafted to said substrate, In this case, said at least one type of nanoparticles is preferably made out of a neutral and resorbable material arranged to interact with the upper layers of the epidermis and release said at least one active ingredient in the targeted organs of said patient.

In this case, said neutral and resorbable material can be made out of a polymer or copolymer of the aliphatic polyester type chosen, for example, in the group including polylactic acid and polyglycolic acid.

In compliance with the invention, said nanoparticles have preferably a size between 70 nm and 300 nm.

An additional characteristic of the invention is defined by the fact that said at least one ligand is an o-nitrobenzyl derivative chosen in the group including 4-[4-(1-hydroxyethyl)-2-methoxy-5-nitrophenoxy] butanoic acid and 4-[4-(1-aminoethyl)-2-methoxy-5-nitrophenoxy] butanoic acid.

Moreover, the device according to the invention is also characterized in that said control means comprise at least one light-emitting diode with a predetermined wavelength arranged in front of said at least one tank and powered by at least one battery.

The device according to the invention comprises preferably as many light-emitting diodes as tanks, these light-emitting diodes being connected with each other in parallel and being able, at least for some of them, to deliver an identical wavelength.

In compliance with an additional characteristic of the present device, said control means comprise at least said battery, at least one microprocessor, and at least one transmitter/receiver coupled with a radio antenna arranged to receive signals from a remote transmitter/receiver that is itself arranged to program in a personalized way the administration of said at least one active ingredient to the patient.

Said radio antenna uses preferably the radio frequency identification (RFID) technology.

Furthermore, said electronic circuit is characterized in that it is integrated in a support superimposed and bound to said substrate, said support being preferably flexible and made out of a biocompatible and light-conducting material.

According to an additional characteristic of the present device, said control means comprise at least one counter that allows determining the illumination time of said substrate and thus controlling the released quantity of said at least one active ingredient.

In another embodiment variant, said substrate can comprise at least one passive tank containing at least one active ingredient arranged to be administered to said patient in a continuous and uncontrolled way.

BRIEF DESCRIPTION OF THE DRAWINGS

The present invention and its advantages will be better revealed in the following description of an embodiment given as a non limiting example, in reference to the drawings in appendix, in which.

DETAILED DESCRIPTION OF THE PREFERRED EMBODIMENTS

Referring to the figures, the transdermal device 1 according to the invention allows administering in a controlled way at least one active ingredient to a patient through a dermal surface or a mucous membrane.

Figure 1:
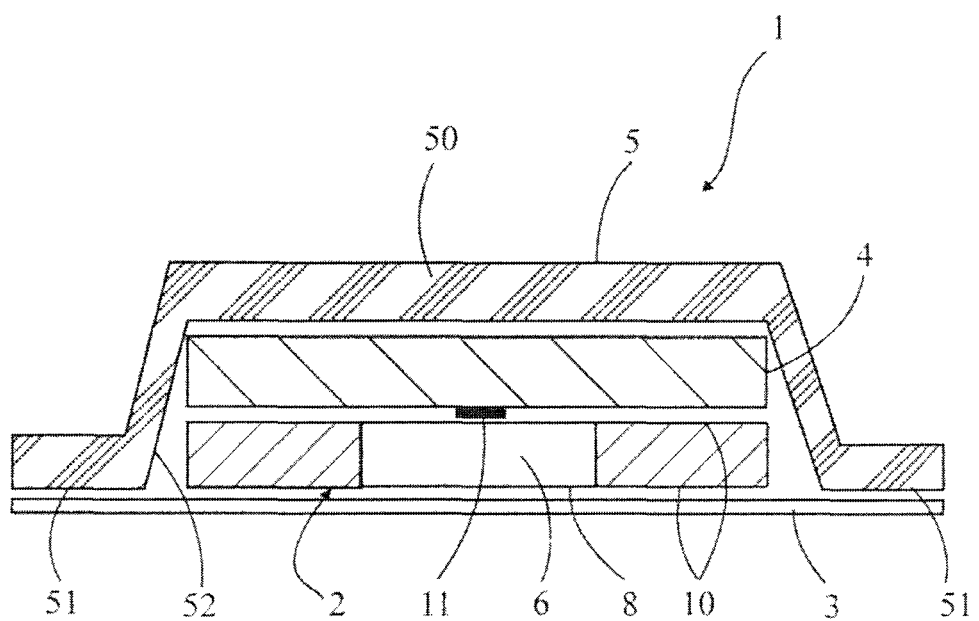
FIG. 1 is a magnified cross-sectional view of the transdermal device according to the invention.

As illustrated in FIG. 1, the transdermal device 1 includes a substrate 2 arranged to be applied against said dermal surface or said mucous membrane of said patient after having removed a protective film 3 that covers the bottom side of the transdermal device 1 during packaging and storage.

Figure 2:
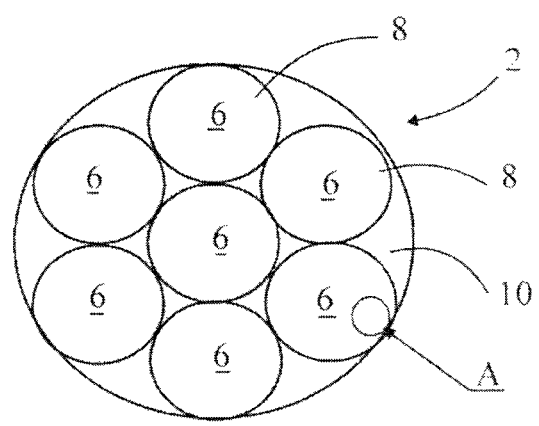
FIG. 2 is a top view of the interchangeable module of the device according to the invention comprising several active ingredient tanks.
Figure 2A:
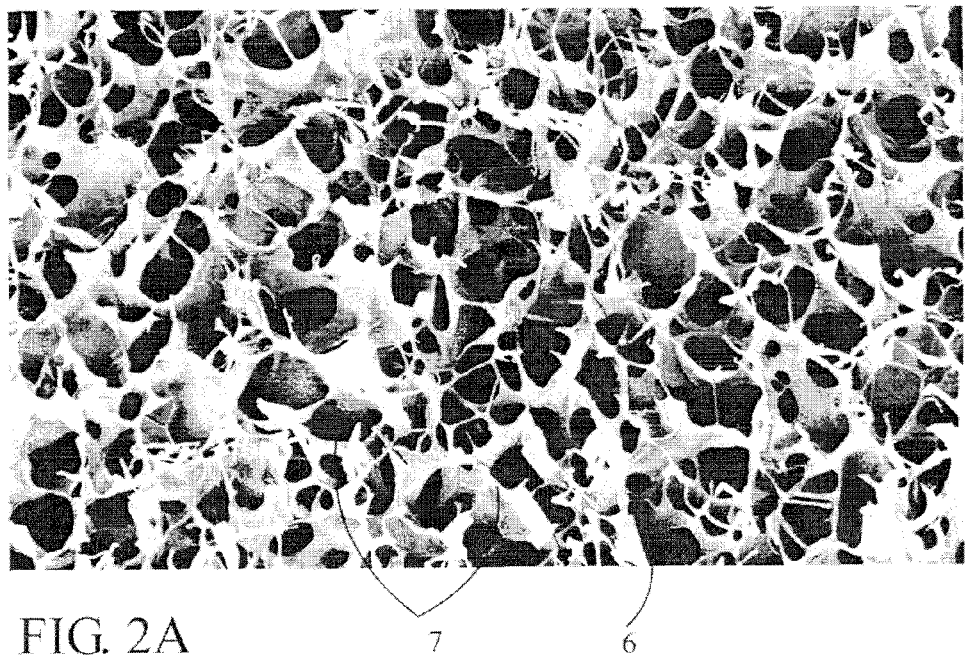
FIG. 2A is a greatly magnified view of detail A of FIG. 2 showing the three-dimensional structure of one of the tanks.

In compliance with the present invention, the substrate 2 comprises at least one porous matrix 6 with a three-dimensional structure comprising a plurality of pits 7 (refer to FIGS. 2 and 2A) organized in a sponge-like fashion and whereto at least one active ingredient is grafted by means of at least one photolabile ligand. Such matrix 6 thus defines at least one three-dimensional tank 8 for said at least one active ingredient, which will be contained in pits 7 after coupling it by grafting by means of said photolabile ligand. The porous matrix 6 is advantageously made out of a biodegradable and biocompatible polymer chosen in the family of the polysaccharides, and more specifically among chitin and chitosan, which allow constructing stable, high-quality and reproducible three-dimensional pit structures using industrial manufacturing processes, therefore at low and controlled production costs, and which show natural antifungal and antibacterial properties indispensable for the concerned applications. An example of a chitosan sponge intended for releasing active ingredients is in particular described in the publication "Chitosan Sponges to Locally Deliver Amikacin and Vancomycin" by Scott P. Noel MS & Co, published on Mar. 10, 2010.

In the illustrated embodiment variant, the substrate 2 comprises seven porous matrices 6 arranged to define each one thank 8 that can contain each a same concentration of a same active ingredient, or various concentrations of a same active ingredient, or various active ingredients or a combination of identical and different active ingredients, according to the nature of the photolabile ligand grafted in each of the matrices 6. This allows adapting closely the transdermal device 1 to the needs of the patient and to the dosage prescribed by the physician. Of course, other configurations wherein the substrate 2 comprises between one an N matrices 6 can also be considered.

In addition to the normal use of the transdermal device 1 according to the invention, the substrate 2 can simultaneously be loaded with active ingredients released without any control. In this case, one or several so-called passive tanks 8 are loaded directly with active ingredients, by absorption of a solution that contains the active ingredient(s) an/or the nanoparticles which themselves contain the active ingredient(s), without bond and without grafting. This way, the administration of the active ingredient(s) to the patient takes place continuously, as with a classical passive patch. The invention advantageously allows, on a same substrate 2, to use simultaneously the two active ingredient release modes: an active mode and a passive mode. This combination allows for example administering continuously and without control a compound A (A being an active ingredient, a nanoparticle loaded with an active ingredient or a penetration agent) while releasing in a controlled way a compound B (or nanoparticle) bound to matrix 6 by means of the photolabile ligand. One can also provide for example for three active matrices 6, the rest of the matrices 6 being passive.

According to another characteristic of the invention, the photolabile ligand is preferably chosen among an o-nitrobenzyl derivative such as for example 4-[4-(1-hydroxyethyl)-2-methoxy-5-nitrophenoxy] butanoic acid or 4-[4-(1-aminoethyl)-2-methoxy-5-nitrophenoxy] butanoic acid. Each ligand is bonded or grafted by one of its ends to matrix 6 defining a tank 8 by means of a non-photolabile covalent bond, and by the other of its ends to the active ingredient or to the nanoparticle containing said active ingredient by means of a photolabile covalent bond, that is to say that this bond can be broken by a light pulse whose wavelength depends on the nature of said ligand.

Figure 3:
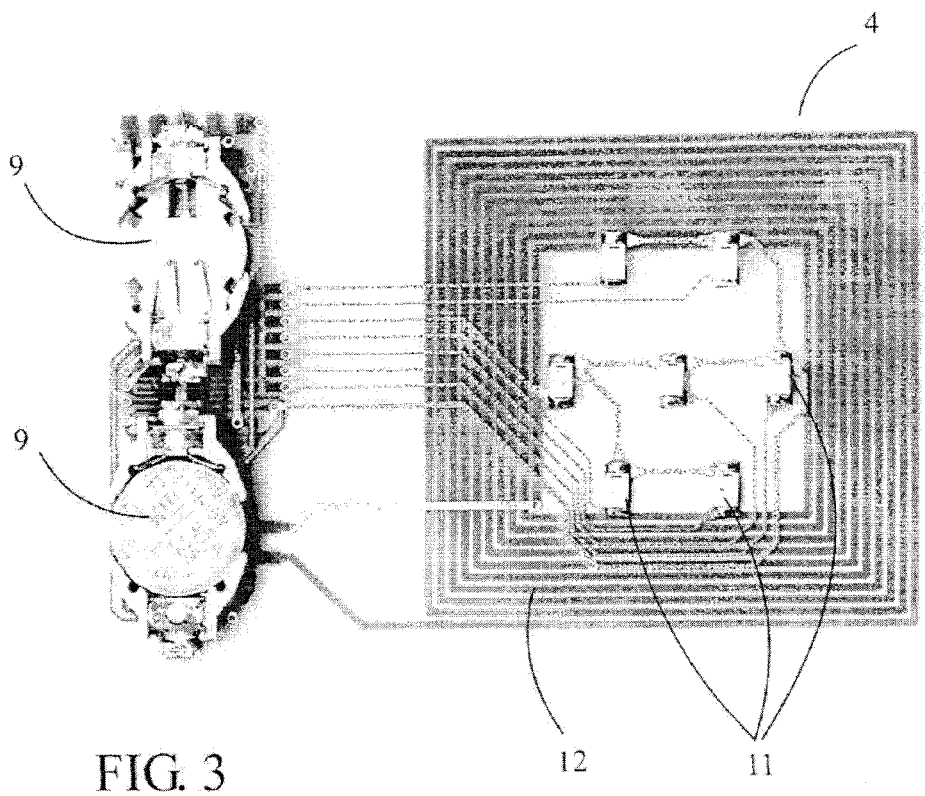
FIG. 3 is a view of the bottom side of the support integrating the electronic section of the device according to the invention, against which the interchangeable module of FIG. 2 will be arranged.

The transdermal device 1 comprises for that purpose a preferably flexible support 4 superimposed and bound to said substrate 2 and integrating, in the illustrated example, seven light-emitting diodes 11 (refer to FIGS. 1 and 3) powered by at least one battery 9, operated by control means, connected with each other in parallel, and intended for being arranged opposite to each matrix 6. They allow sending in a direction perpendicular to said matrices 6 a light pulse with a given wavelength to break the photolabile covalent bond between the ligand and the active ingredient or the nanoparticle containing the active ingredient. The active ingredient or the nanoparticle thus released from the ligand, which remains bonded to matrix 6, can then pass through the porous structure of the latter to be diffused towards the dermal surface or mucous membrane of said patient. The support 4 is preferably made out of a material having low absorption in the wavelength of the light-emitting diodes 11 such as, for example, a biocompatible plastic, so that most of the light energy generated by the light-emitting diodes 11 actually reaches said photolabile ligand.

The light-emitting diodes 11 can moreover be chosen in order to deliver each the same wavelength or different wavelengths. When various active ingredients are coupled to substrate 2 by means of various photolabile ligands that react to different wavelengths, a selective release of a given active ingredient with respect to another one can be achieved by selecting appropriately the wavelength of the light pulse applied to said substrate 2 and by activating the appropriate light-emitting diode(s) 11. On the other hand, even though, in the illustrated example, the transdermal device 1 comprises as many light-emitting diodes 11 as matrices 6, other variants can also be considered, such as for example those comprising more than one light-emitting diode 11 arranged opposite to a same matrix 6.

The transdermal device 1 moreover comprises an occlusive film 5 made for example out of a composite material comprising a polyester layer lined with a layer out of aluminum or any equivalent material. The lower side 52 of the occlusive film 5 is covered, at least on its peripheral areas 51, with a biocompatible adhesive allowing the adhesion of the transdermal device 1 on a dermal surface or mucous membrane of said patient, while the central area 50 of said occlusive film 5 covers and protects the set formed by the substrate 2 and the support 4 in particular against light and drying out with regard to the substrate 2.

Furthermore, the substrate 2 can advantageously be bonded to support 4 by means of a non-permanent adhesive such as in particular a silicone layer 10 (refer to FIG. 2) distributed among the various matrices 6 and also allowing its adhesion to the skin or a mucosa of the patient. In this case, the substrate 2 defines advantageously an interchangeable module that can easily be replaced by the patient with another substrate 2. So, when the patient wants for example to replace a used substrate 2, whose total quantity of initially contained active ingredient has been administered to him, with a new substrate 2 containing a complete dose of active ingredient, he simply has to unstick the transdermal device 1 by removing the occlusive film 5 from his skin, to remove the used substrate 2 from the support 4 before re-positioning a new substrate 2 on the support 4. The transdermal device 1 whose support 2 has been renewed can then be applied again on the skin of the patient using a new occlusive film 5. Such a structure, which allows keeping the electronic section of the transdermal device 1 and to renew only the part loaded with active ingredient(s) leads advantageously to a significant costs reduction for the patient. In this case, in order to facilitate the replacement operation of the support 2, indexing means that allow ensuring the perfect positioning of the matrices 6 opposite to the light-emitting diodes 11 can moreover be provided, such as for example male and female elements respectively located on the substrate 2 and on the support 4, intended to be fitted together by the user.

According to another characteristic of the invention, the active ingredient can be contained or encapsulated in nanoparticles bonded or grafted each to one of the ends of a ligand by means of a photolabile covalent bond, the other end of said ligand being grafted to matrix 6 by means of a non-photolabile covalent bond. Said nanoparticles are made preferably out of a polymer or a copolymer of the aliphatic polyester type, neutral and resorbable, such as for example polylactic acid or polyglycolic acid. They have preferably a size between 70 nm and 300 nm and are able to interact with the upper layers of the epidermis of the patient in order to release said at least one active ingredient in the targeted organs of said patient. The nanoparticles allow advantageously to increase significantly the quantity of active ingredient that can be administered transdermally in comparison with the classical transdermal devices wherein the active ingredient is bonded directly onto the substrate.

In the illustrated embodiment variant, the transdermal device 1 comprises moreover an electronic circuit integrated in the support 4, powered by said at least one battery 9, connected to said light-emitting diodes 11 and to at least one radio antenna 12 using the radio frequency identification (RFID) technology. This electronic circuit furthermore comprises at least one microprocessor and a transmitter/receiver coupled with the radio antenna 12 to receive signals from a remote transmitter/receiver that is itself arranged to program the microprocessor in a personalized way, for example from a medical practice in order to administer said at least one active ingredient to said patient according to a defined dosage. The emission of a light pulse by at least one of said light-emitting diodes 11 in order to diffuse individually or jointly one or several active ingredients is triggered or not by the microprocessor program. The physician can at any time remotely control the method of administration of said at least one active ingredient to said patient, in particular the dose and the moment, modify the dosage and adapt it to improve the therapeutic effects of the treatment for the patient.

Moreover, the transdermal device 1 according to the invention comprises at least one counter (not illustrated) integrated in said electronic circuit to determine the illumination time of said substrate 2 according to the quantity of active ingredient to be administered. This data is processed by the integrated microprocessor. The physician can determine, using a specific software, the illumination time required to release a desired quantity of active ingredient. If he deems necessary, the physician can intervene remotely to modify this illumination time in order to modify the doses or the type(s) of the administered active ingredients.

Possibilities For Industrial Application:

This description shows clearly that the invention allows reaching the goals defined, thanks to a transdermal device 1 comprising several tanks independent from each other, whose three-dimensional structure allows storing a large volume of active ingredient(s), and that can be loaded, according to the case, either each with a same dosage of a same active ingredient, or with different dosages of a same active ingredient, or with different active ingredients, or with a combination of the foregoing.

Such transdermal device 1 allows administering successively identical dosages or different dosages of a same active ingredient, or jointly or successively at least two different active ingredients, in order to improve the therapeutic effects by playing on the synergy of the active ingredients. Moreover, the transdermal device 1 according to the invention is arranged to exchange data with a central management device such as the computer of the prescribing physician. The latter can therefore be informed in real time of the doses and nature of the active ingredient(s) actually delivered to the patient and control the transdermal device 1 remotely. He can this way for example trigger the administration of an active ingredient rather than that of another by causing its release with the operation of a given light-emitting diode 11. If necessary, the physician can also reduce or stop the administration of the active ingredient by reducing or stopping the operation of one or several light-emitting diodes 11 and therefore limit as much as possible all possible side effects due to too important doses.

Moreover, encapsulating the active ingredients in nanoparticles allows dissociating them from the photolabile ligands and therefore extending ad infinitum the range of active ingredients liable to be grafted to the substrate 2, as their compatibility with the photolabile ligands of the prior art is not required any more.

On the other hand, the areas of application of the transdermal device 1 according to the invention are not restricted to pharmacy, but extend also, among others, to cosmetics and to the veterinary field.

The present invention is not restricted to the example of embodiment described, but extends to any modification and variant which is obvious to a person skilled in the art while remaining within the scope of the protection defined in the attached claims.

The invention claimed is:

1. A transdermal device (1) for controlled administration to a patient of at least one active ingredient through a dermal surface or a mucous membrane, the transdermal device (1) comprising:
   at least one substrate (2) arranged to be applied against he dermal surface or the mucous membrane,
   the at least one active ingredient being grafted to the substrate (2) by at least one photolabile ligand,
   in addition, the transdermal device (1) comprising at least one light source (11) operated by control means arranged to generate light pulses of a predetermined wavelength intended to break the at least one ligand and release the at least one active ingredient from the substrate (2),
   wherein the substrate (2) comprises at least one porous matrix (6) with a three-dimensional structure comprising a plurality of pits (7) organized in a sponge-like fashion and constructed of a polymer chosen between chitin and chitosan, the matrix (6) defines at least one three-dimensional tank (8), and the at least one active ingredient is contained and grafted.

2. The transdermal device (1) according to claim 1, wherein the substrate (2) comprises a plurality of matrices (6) each arranged to define a tank (8) able to contain one of a same concentration of a same active ingredient, or different concentrations of a same active ingredient or different active ingredients.

3. The transdermal device (1) according to claim 1, wherein the substrate (2) forms an interchangeable module connected with the transdermal device (1) by a non-permanent adhesive.

4. The transdermal device (1) according to claim 1, wherein the at least one active ingredient is encapsulated in at least one type of nanoparticle bonded with the at least one ligand which is grafted to the substrate (2).

5. The transdermal device (1) according to claim 4, wherein the at least one type of nanoparticle is made out of a neutral and resorbable material arranged to interact with the upper layers of an epidermis and release the at least one active ingredient in the targeted organs of the patient.

6. The transdermal device (1) according to claim 5, wherein the neutral and resorbable material is made out of a polymer or copolymer of an aliphatic polyester type.

7. The transdermal device (1) according to claim 6, wherein the polymer or copolymer is selected from the group consisting of polylactic acid and polyglycolic acid.

8. The transdermal device (1) according to claim 4, wherein each of the at least one type of nanoparticle has a size between 70 nm and 300 nm.

9. The transdermal device (1) according to claim 1, wherein the at least one ligand is an o-nitrobenzyl derivative selected from the group consisting of 4-[4-(1-hydroxyethyl)-2-methoxy-5-nitrophenoxy] butanoic acid and 4-[4-(1-aminoethyl)-2-methoxy-5-nitrophenoxyl] butanoic acid.

10. The transdermal device (1) according to claim 1, wherein the control means operate at least one light-emitting diode (11) with a predetermined wavelength arranged in front of the at least one tank (8) and powered by at least one battery (9).

11. The transdermal device (1) according to claim 10, wherein the transdermal device (1) comprises as many light-emitting diodes (11) as tanks (8) and the light-emitting diodes (11) are connected in parallel with one another.

12. The transdermal device (1) according to claim 11, wherein at least some of the light-emitting diodes (11) deliver an identical wavelength.

13. (NEVV) The transdermal device (1) according to claim 10, wherein the control means comprise at least the battery (9), at least one microprocessor and at least one transmitter/receiver coupled with a radio antenna (12) arranged to receive the signals from a remote transmitter/receiver that is arranged to program, in a personalized way, the administration of the at least one active ingredient to the patient.

14. The transdermal device (1) according to claim 13, wherein the radio antenna (12) uses radio frequency identification (RFID) technology.

15. The transdermal device (1) according to claim 13, wherein the electronic circuit is integrated in a support (4) superimposed and bound to the substrate (2).

16. The transdermal device (1) according to claim 15, wherein the support (4) is flexible and made out of a biocompatible and light-conducting material.

17. The transdermal device (1) according to claim 16, wherein the control means comprise at least one counter that allows determination of an illumination time of the substrate (2) and thereby controls a released quantity of the at least one active ingredient.

18. The transdermal device (1) according to claim 1, wherein the substrate (2) comprises at least one passive tank containing at least one active ingredient arranged to be administered to the patient in a continuous and uncontrolled way.

* * * * *